(12) United States Patent
Dhillon

(10) Patent No.: US 7,207,714 B1
(45) Date of Patent: Apr. 24, 2007

(54) EXTENSIBLE POSITIONING AND TARGETING APPARATUS FOR A BEAM EMITTING SOURCE

(76) Inventor: Harkeerat Dhillon, 6366 Harwarden Dr., Riverside, CA (US) 92506

( * ) Notice: Subject to any disclaimer, the term of this patent is extended or adjusted under 35 U.S.C. 154(b) by 0 days.

(21) Appl. No.: 11/441,551

(22) Filed: May 26, 2006

(51) Int. Cl.
*H05G 1/00* (2006.01)

(52) U.S. Cl. ...................... 378/204; 378/205

(58) Field of Classification Search ............ 378/65, 378/145, 147, 204, 205
See application file for complete search history.

(56) References Cited

U.S. PATENT DOCUMENTS

| | | | |
|---|---|---|---|
| 1,117,266 A | 11/1914 | Snook | 378/151 |
| 2,217,308 A | 10/1940 | Cox | 378/206 |
| 2,551,703 A | 5/1951 | Puls | 378/205 |
| 2,659,824 A | 11/1953 | Burnham | 378/206 |
| 3,649,835 A | 3/1972 | Brankenbrough et al. | 378/148 |
| 3,745,344 A | 7/1973 | Updegrave | 378/170 |
| 4,150,296 A | 4/1979 | Edeland et al. | 378/170 |
| D254,805 S | 4/1980 | Edeland | D24/161 |
| D283,157 S | 3/1986 | Maldonado et al. | D24/161 |
| 4,993,057 A | 2/1991 | Runnells | 378/197 |
| 2005/0047550 A1 | 3/2005 | Yao et al. | 378/170 |

*Primary Examiner*—Courtney Thomas
(74) *Attorney, Agent, or Firm*—Gene Scott; Patent Law & Venture Group

(57) ABSTRACT

A positioning and targeting apparatus is attached to a beam emitting source having a beam central axis. The apparatus has an attachment collar enabled for securement to the emitting source. A lateral supporting member is engaged with the attachment collar and extends in an axial direction. A radial supporting member is engaged with the lateral supporting member and terminates on the beam central axis. A pointer is, in turn, engaged with the radial supporting member and positioned along the beam central axis. The pointer provides at least one axially telescoping segment and a locking nut for fixing the telescoping segment at a selected telescoping position relative to a base segment of the pointer. The radial supporting member and the pointer are made of material invisible to the source's beam.

6 Claims, 3 Drawing Sheets

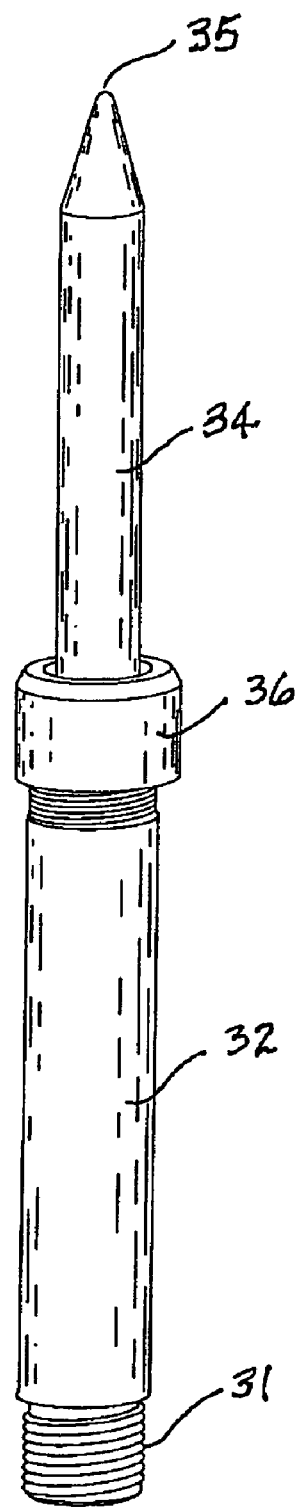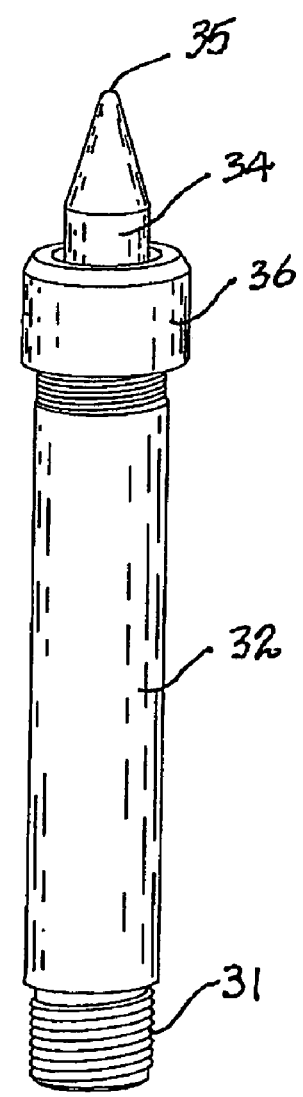
*Fig. 3*  *Fig. 4*

EXTENSIBLE POSITIONING AND TARGETING APPARATUS FOR A BEAM EMITTING SOURCE

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

REFERENCE TO A "MICROFICHE APPENDIX"

Not applicable.

BACKGROUND OF THE INVENTION

1. Field of the Present Disclosure

This disclosure relates generally to targeting devices for radiographic applications, and more particularly to a pointer-handle combination device that is easily attached to an emitting source, which is centered within the beam field, is extensible and which may remain in place during exposures or may be pivoted to one side during exposures.

2. Description of Related Art Including Information Disclosed Under 37 CFR 1.97 and 1.98

Yao et al., U.S. 2005/0047550, discloses a dental x-ray clamping device with a multi-orientation support made up with an attachable ring pivot and a supporting-frame pivot, which is designed for an all-purpose modularized raying clamp with simplified members in design, in which the ring pivot is provided with a pivoting ring, while the supporting-frame pivot is provided with a pivoting supporting bite frame, and only the supporting bite frame is pivoted to an opening side of a supporting orientation and combined with the ring pivot easily pivoting at a required angle of rotation so as to be located at an orientation so that the center of the ring aligns with that of the opening side of the supporting bite frame and further that the x-ray operation can be performed at the case of the teeth diagnosis or the endodontic treatment using each orientational support on the teeth. Edeland, U.S. Des. 254805, describes a dental holder for X-Ray films. Maldonado et al., U.S. Des. 283157, describes a device for positioning dental X-Ray film. Snook, U.S. Pat. No. 1,117,266, discloses an apparatus, a main frame within which an object to be observed may be placed, of an observation frame on the main frame at the front thereof, an X-ray tube carried by the main frame at the rear thereof, means shielding the operator in front of the observation frame from direct rays from the X-ray tube, and means absorptive of rays of lesser degree including the main frame and the object under observation. Cox, U.S. Pat. No. 2,217,308, discloses a position determining means for an X-ray apparatus which apparatus includes beam confining and directing means; the determining means including a spot-light adapted to throw a beam of light and a source of current therefore, a pivot post, an arm, turnable about the post, supporting the spot-light with the axis of the light beam parallel to the axis of the post, a bracket carrying the post, means for securing the bracket to the apparatus with the post parallel to the axis of the X-ray beam, and at equal distances from the axes of the light and X-ray beams; means for adjusting the post longitudinally relatively to the bracket, means for frictionally resisting turning movement of the arm about the post, and a stop member carried by the post and cooperating with the arm to limit turning movement of the arm when the axes of the beams are substantially coincident. Puls, U.S. Pat. No. 2,551,703, discloses a bracket member comprising a member for attachment to an X-ray machine at a right angle to the axis of the ray of the X-ray machine, a split block having a circular central opening, clamping flanges on the block, a swivel in the central opening adapted to rotate therein, claming flanges having a tightening screw therein on the split block for tightening the block upon the swivel to prevent rotation of the swivel, a slidable graduated shaft adapted to slide in the swivel at right angles to the attaching member, a terminal block at the lower end of the slidable shaft, the terminal block having a central rectangular bore at right angles to the axis of the graduated shaft, a second graduated shaft slidable engagable through the opening in the terminal block, the second shaft at right angles to the first mentioned graduated shaft, a tightening screw upon the terminal block for tightening the second shaft against movement, a split ring, the ring having tightening means for rigidly holding the upper member, the lower most member of the telescopic members being tapered to a point. Burnham, U.S. Pat. No. 2,659,824, discloses a position indicator for an X-ray machine of the type having a casing and a removable nose piece threadedly engaging the casing and through which the X-ray beam passes, comprising a flat ring adapted to be secured to the casing and held thereon by the nose piece, brackets fixedly secured to the ring at diametrically opposed points thereof, and a light projector fixedly mounted on each of the brackets and having its optical axis inclined to the direction of the X-ray beam issuing from the casing, whereby the rays issuing from the projectors interact in the axis of the X-ray beam at a predetermined distance in front of the nose piece. Brackenbrough et al., U.S. Pat. No. 3,649,835, discloses an adjustable radiation shield that fits on the collimator used on X-ray equipment for indicating and adjusting the exact area to be exposed to radiation. A shutter of the collimator is adjustable to indicate by means of a light field the area to be exposed. A plurality of radiopaque metal plates are mounted on a support on the collimator is such relation to the collimator as to be normally out of the way of the light field, but be adjustable to obstruct a selected portion of the light field, enabling the technologist to visualize by the shadow cast by the shield the exact area to be protected from radiation without the knowledge of or inconvenience to the patient. Updegrave, U.S. Pat. No. 3,745,344, discloses an X-ray beam of rectangular cross-section that is produced at the end of a lead-lined rectangular collimating tube. The rectangular tube is aligned with a dental film-holding instrument comprising a bite block, a directing rod attached to the bite block, and a rectangular guide member attached to the directing rod. The alignment is achieved by keying the rectangular guide member to the end of the rectangular collimating tube. Edeland et al., U.S. Pat. No. 4,150,296, discloses a holding device for an X-ray plate adapted for mounting on an X-ray tube comprising a ring mountable on the X-ray tube for turning movement thereon. The ring is supported in a groove formed by two auxiliary rings which can lock the ring in a fixed angular position on the tube. A bar is attached by a detachable fastener assembly attached to the ring in a position in which the bar extends parallel to the axis of the tube. The bar is rotatable around its own axis and is longitudinally displaceable in the fastener assembly. The bar extends forwardly from the fastener assembly and has a front end at which there is detachably supported a throw-away X-ray plate-holder extending at right angles to the bar. An X-ray plate is mounted in a slit in the plate-holder and assumes a position at right angles to the axis of the tube. Runnells, U.S. Pat. No. 4,993,057, discloses a sterilizable removable handle that is associated with an X-ray tube head assembly to permit manipulation of the assembly within a sterile field while avoiding contamination of an operator's hand. Bispedjerg Hospital, WO 2004/034909, discloses a radiographic device with a pointer adapted to point at an object of interest in a radiographic image and to visualize a corresponding reference point on a subject, e.g. a person or an animal being subject to medical examination, thus facilitating the alignment of medical tools. The pointer comprises radiographically visible targeting means, and light emitting aiming means being attached to the targeting means in the pointer. The aiming means emits light in a direction substantially parallel to the electromagnetic mediation towards the subject independent of position of the aiming means in relation to the radiographic device.

The related art described above discloses a range of devices for targeting a therapeutic or diagnostic beam such as an x-ray beam. However, the prior art fails to disclose a combination handle and pointer that may be easily attached to a beam source and positioned on axis, to more easily position the source, and which is invisible to the beam so that it may remain in place during beam transmission. The prior art also fails to teach a linearly extensible pointer for improved targeting of the diagnostic beam. The present disclosure distinguishes over the prior art providing heretofore unknown advantages as described in the following summary.

BRIEF SUMMARY OF THE INVENTION

This disclosure teaches certain benefits in construction and use which give rise to the objectives described below.

A positioning and targeting apparatus is attached to a beam emitting source having a beam central axis. The apparatus has an attachment collar enabled for securement to the emitting source. A lateral supporting member is engaged with the attachment collar and extends in an axial direction. A radial supporting member is engaged with the lateral supporting member and terminates on the beam central axis. A pointer is, in turn, engaged with the radial supporting member and positioned along the beam central axis. The pointer provides at least one axially telescoping segment and a locking nut for fixing the telescoping segment at a selected telescoping position relative to a base segment of the pointer. The radial supporting member and the pointer are made of material invisible to the source's beam.

A primary objective inherent in the above described apparatus and method of use is to provide advantages not taught by the prior art.

Another objective is to provide a combination handle and pointer for adjusting a fluoroscope or similar medical device to a desired position relative to a patient.

A further objective is to provide such a handle and pointer that is axially extensible so as to more accurately direct and position the fluoroscope's beam.

A still further objective is to provide such a handle and pointer that need not be moved out of the beam during energy exposures.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWING(S)

Illustrated in the accompanying drawing(s) is at least one of the best mode embodiments of the present invention In such drawing(s):

FIG. 3 is a perspective view of a pointer thereof shown in an extended configuration; and FIG. 4 is a perspective view of the pointer thereof shown in a retracted configuration.

DETAILED DESCRIPTION OF THE INVENTION

The above described drawing figures illustrate the described apparatus and its method of use in at least one of its preferred, best mode embodiment, which is further defined in detail in the following description. Those having ordinary skill in the art may be able to make alterations and modifications what is described herein without departing from its spirit and scope. Therefore, it must be understood that what is illustrated is set forth only for the purposes of example and that it should not be taken as a limitation in the scope of the present apparatus and method of use.

Figure 2:
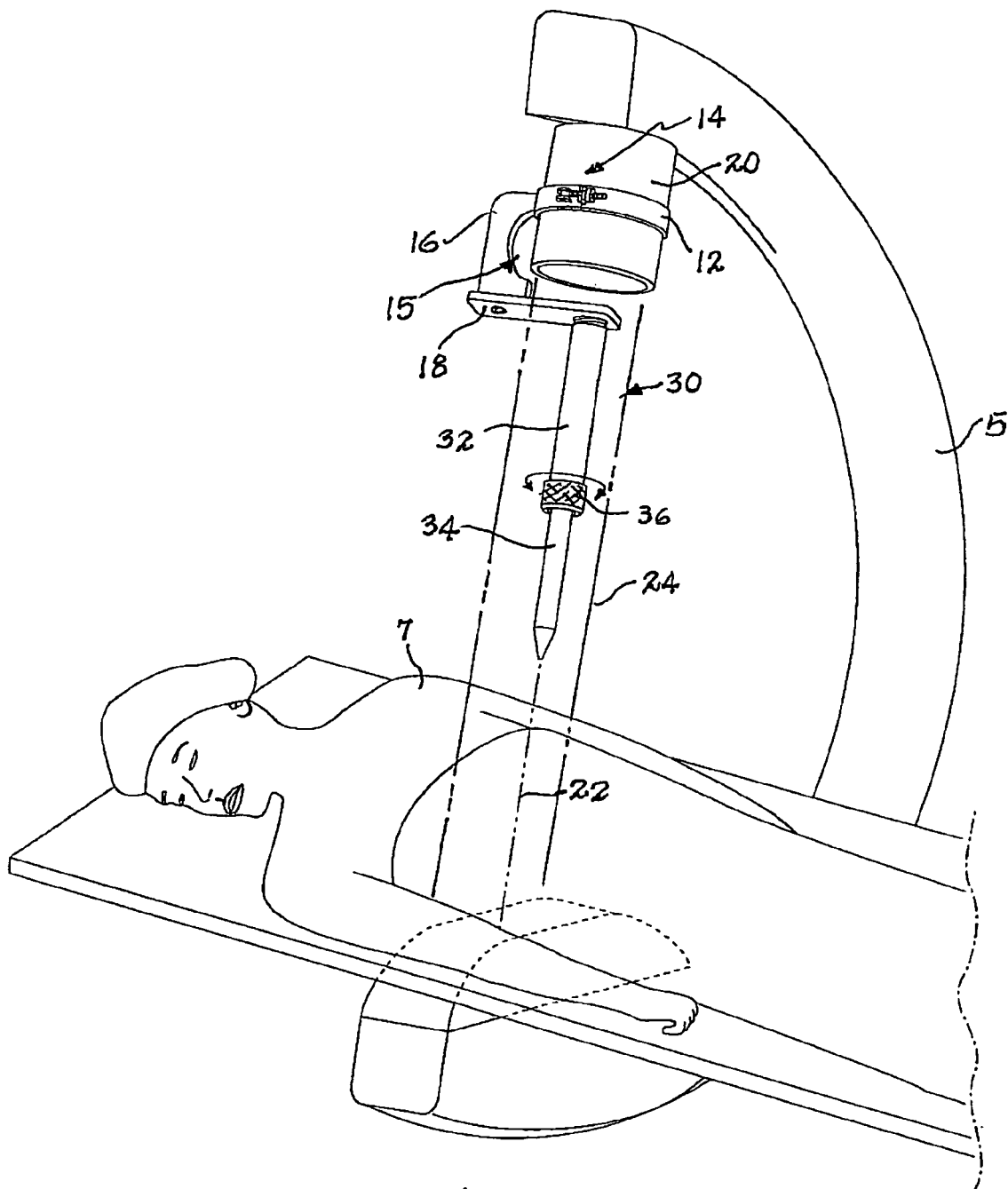
FIG. 2 is a further perspective view thereof as applied to a patient.

Described now in detail is a positioning and targeting apparatus 10 used with a beam emitting source 20 such as an x-ray machine or a fluoroscope 5. The beam source 20 has a beam central axis 22 as shown in FIG. 2, an imaginary line that is positioned at the center of the emitted beam 24 and is directed in parallel to the path of the beam 24. The path of the beam 24 is denoted by phantom lines in FIG. 2.

Figure 1:
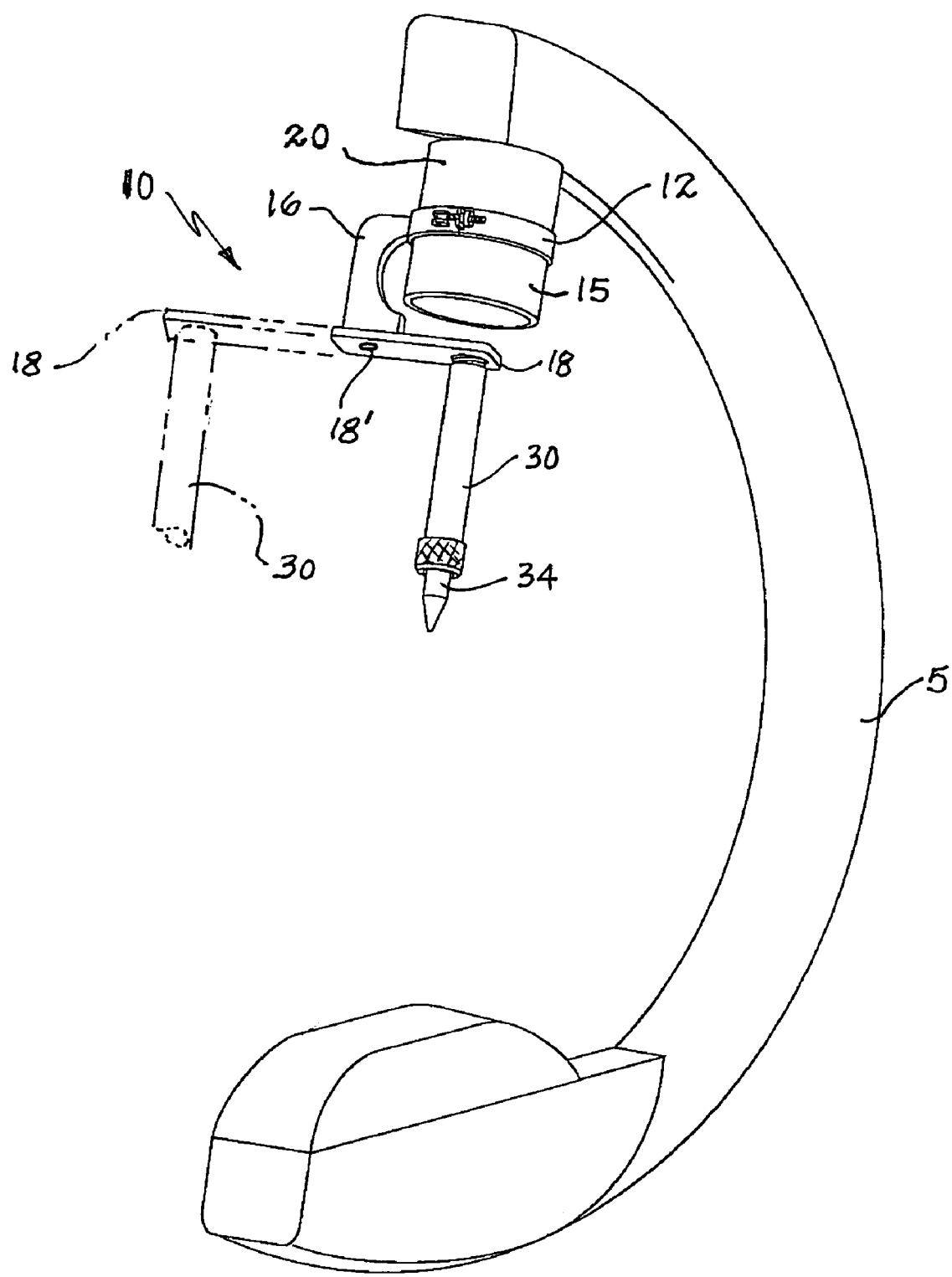
FIG. 1 is a perspective view of the presently described apparatus as applied to a fluoroscope.

The targeting apparatus 10 has an attachment collar 12 with fastening means 14 for securing it to the emitting source 20 as best seen in FIG. 2. The fastening means 14 may be any combination of common fastener hardware such as the pivoted screw, dual mounting ears and nut shown in FIGS. 1 and 2. Such a collar fastener is very well known in the art. A lateral supporting member 16 is engaged at one of its ends with the attachment collar 12 and extends in the axial direction as shown. A radial supporting member 18 is engaged at one of its ends with the other end of the lateral supporting member 16, and the radial supporting member 18 terminates at the beam central axis 22. Whereas the lateral supporting member 16 is to one side of the beam 24 and therefore is not immersed in the beam 24, the radial supporting member 18 protrudes radially into the beam 24, as shown in FIG. 2 and is therefore immersed within the beam 24 during the pointing step, but may be rotated about pivot 18' out of the beam 24, as shown in FIG. 1 during the exposure step. A pointer 30 is engaged, preferably by threads 31 in a threaded engagement with the radial supporting member 18 and is oriented along the beam central axis 22, directed from the radial supporting member 18 toward a patient 7.

Preferably, the pointer 30 comprises a base segment 32 and a telescoping segment 34, the later axially engaged within the former and slidingly fitted therewithin so as to enable coaxial linear extension of the telescoping segment 34 from the base segment 32. The base segment preferably provides a tightening nut 36 (a means for fixing) such as a collet collar, which is well known in the art, for setting the telescoping segment 34 at a selected extension from the base segment 32. More than one telescoping segment 34 may be fitted, one within the next, in the same manner as described above to achieve a longer extension of the pointer 30.

The pointer 30 and the radial supporting member 18 are made of a material invisible to the particular energy beam 24 that is being used. For instance, a fluoroscope beam is not disturbed by an engineering polymer such as polycarbonate. Therefore, the pointer 30 does not influence the energy beam 24. Because of this fact, the pointer 30 is usable as a handle in moving the beam source 20, which is typically mounted on a mechanism that allows the beam source 20 to be positioned as desired simply by manual forces, while the pointer identifies where the exact center of the beam 24 will be located. This is extremely valuable when time does not allow for multiple exposures or when the energy dose to the patient must be kept to a minimum. Both of these parameters are important in every medical situation. When beam exposure on a precise point on the anatomy, is critical, as for instance in surgery on a hand, the fact that the pointer preferably has a conical and pointed terminal end 35, see FIGS. 3 and 4, gives the technician the advantage of being able to place the terminal end 35 of the pointer 30 in near contact with a precise point on the anatomy so that an exposure may be taken with great precision.

Preferably, the lateral supporting member 16 is positioned in line with the attachment collar 12 so that the radial supporting member 18 is as short as possible thereby providing maximum stability to the pointer 30, i.e., a minimum of movement of the pointer 30 due to its cantilevered support. Therefore, the lateral supporting member 16 is closely adjacent, nearly touching, or in fact, touching, the beam emitting source 20 when the attachment collar 12 is mounted on the beam emitting source 20. This specific juxtaposition of elements makes it difficult to mount the collar 12 on the source 20 since the lateral supporting member 16 cannot be fully grasped due to the lack of finger clearance between it and the source 20. Therefore, preferably, a hand-sized cutout 15 is formed on the lateral supporting member 16 to enable proper grasping of the apparatus. See FIGS. 1 and 2.

In use, the apparatus is gripped with, for instance, a left hand around the cutout 15 in the lateral supporting member 16 so as to bring the collar 12 up to and around the beam source 20 and then the collar 12 is fastened about the beam source 20. Next, the pointer 30 is used as a handle to bring the beam source 20 into a correct attitude to direct the beam 24 toward the target (a portion of the patient's anatomy). Next, the tightening nut 36 is loosened and the telescoping segment 34 is extended as desired toward the patient 7, and specifically toward the exact point that it is desired to radio image. When this is completed, the tightening nut 36 is retightened and the pointer may be used again to fine-tune the location of the beam 24.

The enablements described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. A positioning and targeting apparatus for use with a beam emitting source having a beam central axis, the apparatus comprising: an attachment collar enabled for securement to the emitting source; a lateral supporting member engaged with the attachment collar and extending therefrom in an axial direction; a radial supporting member engaged with the lateral supporting member, the radial supporting member terminating on the beam central axis; and a pointer engaged with the radial supporting member, the pointer oriented along the beam central axis, the pointer providing at least one axially telescoping segment and a means for fixing the at least one telescoping segment at a selected telescoping position relative to a base segment of the pointer; the radial supporting member and the pointer made of material invisible to an energy beam.

2. The apparatus of claim 1 wherein the lateral supporting member is positioned in line with the attachment collar and is thereby closely adjacent to the beam emitting source when the collar is mounted on the beam emitting source, the lateral supporting member providing a hand-sized cutout therein for receiving a hand holding the lateral supporting member when fastening the collar to the beam emitting source.

3. The apparatus of claim 1 wherein the at least one telescoping segment, is a single telescoping segment, the telescoping segment slidingly fitted within the base segment thereby enabling coaxial linear extension therefrom, the base segment providing a tightening collar for fixing the telescoping segment at a selected extension from the base segment.

4. A positioning and targeting apparatus comprising: a beam emitting source having a beam central axis; an attachment collar secured to the emitting source; a lateral supporting member engaged with the attachment collar and extending therefrom in an axial direction; a radial supporting member engaged with the lateral supporting member, the radial supporting member terminating on the beam central axis; and a pointer engaged with the radial supporting member, the pointer oriented along the beam central axis, the pointer providing at least one axially telescoping segment and a means for fixing the at least one telescoping segment at a selected telescoping position relative to a base segment of the pointer; the radial supporting member and the pointer made of material invisible to an energy beam.

5. The apparatus of claim 4 wherein the lateral supporting member is positioned in line with the attachment collar and is thereby closely adjacent to the beam emitting source when the collar is mounted on the beam emitting source, the lateral supporting member providing a hand-sized cutout therein for receiving a hand holding the lateral supporting member when fastening the collar to the beam emitting source.

6. The apparatus of claim 4 wherein the at least one telescoping segment, is a single telescoping segment, the telescoping segment slidingly fitted within the base segment thereby enabling coaxial linear extension therefrom, the base segment providing a tightening collar for fixing the telescoping segment at a selected extension from the base segment.

* * * * *